United States Patent
Sivadas

(10) Patent No.: US 9,672,758 B2
(45) Date of Patent: Jun. 6, 2017

(54) KIT FOR REPLICATING AN IMPLANTABLE PROSTHETIC DEVICE

(75) Inventor: Sujit Sivadas, Bridgewater, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 391 days.

(21) Appl. No.: 13/456,719

(22) Filed: Apr. 26, 2012

(65) Prior Publication Data

US 2013/0289733 A1  Oct. 31, 2013

(51) Int. Cl.
*A61F 2/38* (2006.01)
*A61B 1/00* (2006.01)
*G09B 23/30* (2006.01)
*A61F 2/46* (2006.01)

(52) U.S. Cl.
CPC ........... *G09B 23/30* (2013.01); *A61F 2/4684* (2013.01); *A61F 2/3859* (2013.01)

(58) Field of Classification Search
CPC ...... A61F 2002/0072; A61F 2230/0076; A61F 2/2436; A61F 2/4657; A61F 2002/2825; A61F 2002/30515; A61F 2002/30654; A61F 2002/30934; A61F 2002/30948; A61F 2002/3097; A61F 2002/30985; A61F 2002/3863; A61F 2002/3895

USPC .............................................. 623/22.11–22.12
See application file for complete search history.

(56) References Cited

U.S. PATENT DOCUMENTS

| | | | |
|---|---|---|---|
| 4,936,847 A | 6/1990 | Manginelli | |
| 4,950,298 A | 8/1990 | Gustilo et al. | |
| 5,171,282 A * | 12/1992 | Pequignot | A61F 2/3859 623/20.35 |
| 5,824,100 A | 10/1998 | Kester et al. | |
| 6,074,424 A * | 6/2000 | Perrone et al. | 623/20.3 |
| 6,156,069 A * | 12/2000 | Amstutz | 623/22.11 |
| 7,892,288 B2 * | 2/2011 | Blaylock | A61F 2/30734 623/20.15 |
| 2001/0051830 A1 * | 12/2001 | Tuke et al. | 623/22.12 |
| 2004/0006394 A1 * | 1/2004 | Lipman | A61F 2/3868 623/20.29 |

* cited by examiner

*Primary Examiner* — Ann Schillinger
(74) *Attorney, Agent, or Firm* — Lerner, David, Littenberg, Krumholz & Mentlik, LLP

(57) ABSTRACT

A kit for replicating an implantable prosthetic devices includes a model implant, a geometric tool, and an insert. The model implant may include a first curved surface, and the first curved surface may include a first cutout formed. The geometric tool may include a second curved surface having a second cutout. The geometric configuration of the second cutout may be substantially identical to the geometric configuration of the first cutout of the model implant. The insert may be configured to be engaged with both the first cutout and the second cutout.

13 Claims, 7 Drawing Sheets

KIT FOR REPLICATING AN IMPLANTABLE PROSTHETIC DEVICE

BACKGROUND OF THE INVENTION

The present invention relates to a kit for replicating an implantable prosthetic device. More specifically, the kit may include a replica of an implantable prosthesis and a geometric tool for demonstrating a geometric configuration of the replica.

In some replicas of implantable prosthetic devices, certain of the desired physical aspects that may entice a consumer to purchase the corresponding device are difficult to observe and appreciate. A salesperson may merely provide documentation, coupled with a verbal description, showing a particular feature of an implantable prosthesis. However, this approach suffers certain drawbacks, as some consumers require a tactile demonstration of products in order to be persuaded. Additionally, consumers receive various advertisements, documents, and solicitations regarding potential purchases. Thus, any documentation provided may be discarded, lost, or misplaced, thereby rendering the documentation ineffective. There is also the possibility that a consumer may forget much of the verbal portion of a presentation unless he or she has taken notes. Such notes may have been transcribed on the documentation which, as described above, may become lost or discarded.

Therefore, there is a need for a system that demonstrates a geometric configuration of a replica of an implantable prosthetic device that is intuitive and visually apparent to a consumer.

BRIEF SUMMARY OF THE INVENTION

Described herein are a kit and method for replicating an implantable prosthetic device. According to one aspect of the disclosure, the kit may include a model implant including a first curved surface, and the first curved surface may have a first cutout. The kit may also include a geometric tool having a second curved surface, and the second curved surface may have a second cutout. A geometric configuration of the second cutout may be substantially identical to a geometric configuration of the first cutout of the model implant. The kit may also include an insert configured to be engaged with both the first cutout and the second cutout.

In one example, the first curved surface may correspond to a first articular surface of the implantable prosethetic device. The insert may define an insert surface that corresponds to a portion of the first articular surface of the implantable prosethetic device.

The kit may also include a first model implant component that may be engageable with the model implant. The kit may also include a second model implant component that may be engageable with the first model implant component. The model implant, when engaged with the insert, may be a replica of a femoral prosthesis. In one example, the first model implant component may include a cam. In another example, the second model implant component may include a post configured to engage with a femoral stem. At least a portion of the insert surface may coincide with an arc of a circle.

In one implementation, the model implant may include a base portion and an attachment removably coupled to the base portion. The base portion may include at least a portion of a bicondylar knee implant. The attachment may include a unicondylar knee implant engageable with the bicondylar implant. The geometric tool, when engaged with the insert, forms a wheel with a substantially circular circumference.

According to another implementation, a kit for replicating an implantable prosthetic device may include a model implant having a base portion and an attachment. The attachment may include a first curved surface, and the first curved surface may have a first cutout. The kit may also include a geometric tool having a second curved surface, and the second curved surface may have a second cutout. A geometric configuration of the second cutout may be substantially identical to a geometric configuration of the first cutout of the model implant. The kit may also include an insert configured to be engaged with both the first cutout and the second cutout. The kit may also include a first model implant component that may be engageable with the model implant. The kit may also include a second model implant component that may be engageable with the first model implant component. The model implant, when engaged with the insert, may be a replica of a femoral prosthesis.

According to another implementation, a method of using a kit for replicating an implantable prosthetic device may include providing a model implant including a first curved surface, and the first curved surface may have a first cutout. The method may also include providing a geometric tool having a second curved surface, and the second curved surface may have a second cutout. A geometric configuration of the second cutout may be substantially identical to a geometric configuration of the first cutout of the model implant. The method may also include disengaging an insert from one of the first cutout and the second cutout, and engaging the insert with the other one of the first cutout and second cutout.

In one example, the method may also include providing a first model implant component, and engaging the first model implant component with the model implant. The method may also include providing a second model implant component, and engaging the second model implant component with the first model implant component. In one example, the step of engaging includes engaging the insert with the first cutout so that the first curved surface and the insert may form a replica of a femoral prosthesis.

According to another implementation, a replica of an implantable prosthetic device may include a model implant. The model implant may include a first curved surface, and the first curved surface may have a first cutout. The replica may also include an insert removably engageable with the first cutout. The replica may also include a first model implant component engageable with the model implant, and a second model implant component engageable with the first model implant component.

In another example, the model implant, when engaged with the insert, may be a replica of a femoral prosthesis. In another example, the first curved surface may correspond to a first articular surface of the implantable prosthetic device. In another example, the insert may define an insert surface that corresponds to a portion of the first articular surface of the implantable prosthetic device.

DETAILED DESCRIPTION

According to an aspect of the disclosure, a kit for replicating an implantable prosthetic device allows for a geometric configuration of an implantable prosthetic device to be demonstrated. The kit may include a model implant, a geometric tool, and an insert. The model implant may include a first curved surface, and the first curved surface may include a first cutout. The geometric tool may have a second curved surface, and the second curved surface may have a second cutout. The insert may be engaged and disengaged with either the first cutout or the second cutout. In this way, the geometric features of the model implant may be demonstrated by way of the interchangeability of the insert between the model implant and the geometric tool. For example, the geometric tool, when engaged with the insert, may form a geometric shape, such as a cylinder with a substantially circular cross section and two substantially circular faces. The insert may be disengaged with the geometric tool and engaged with the model implant, allowing the shape of the geometric tool to be associated with the shape of the model implant. The model implant, when engaged with the insert, may include a portion that forms an arc of a circle.

Figure 1:
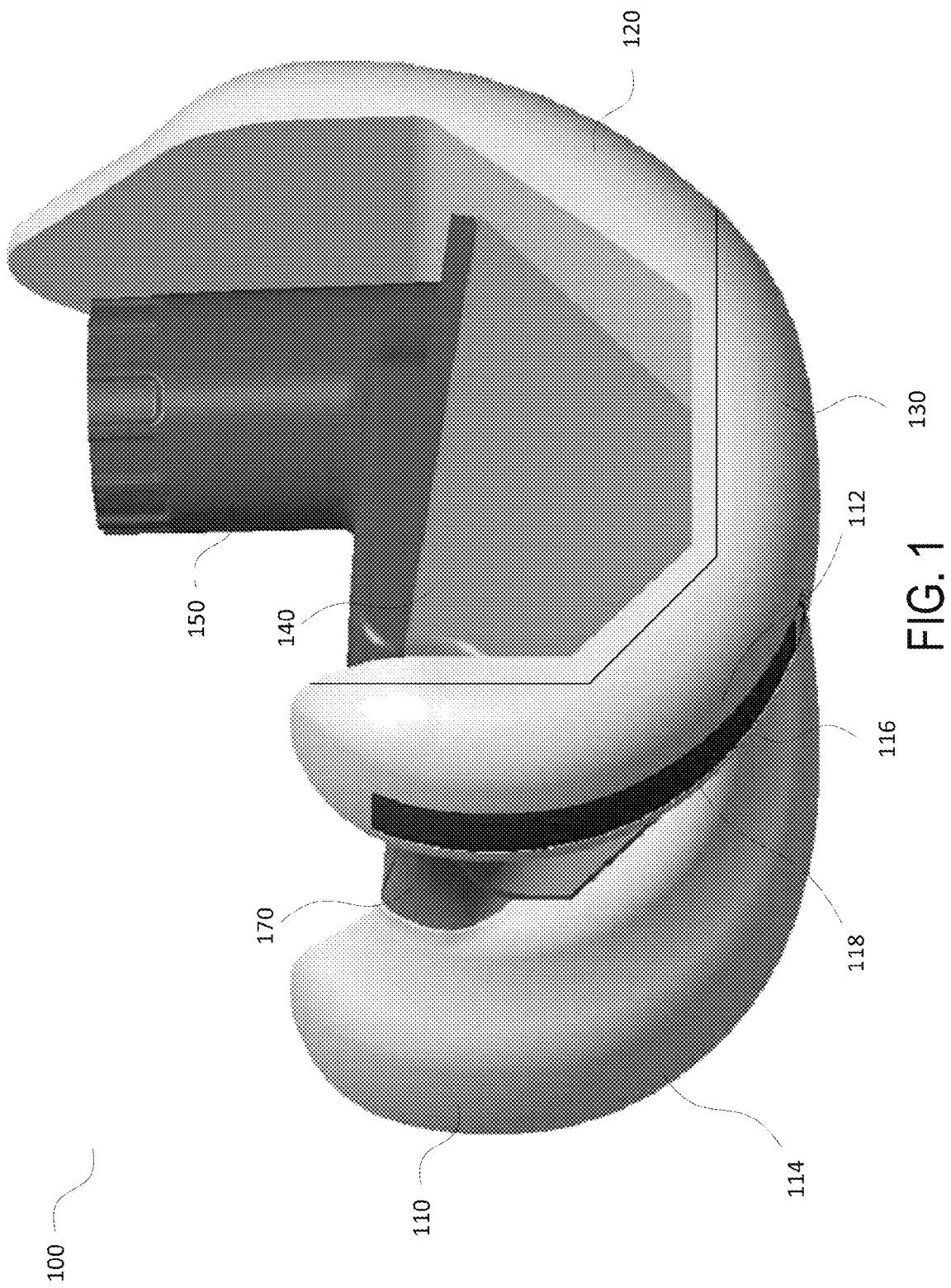
FIG. 1 illustrates a perspective view of a replica of an implantable prosthetic device according to one aspect of the disclosure.

FIG. 1 illustrates a perspective view of replica 100 of an implantable prosthetic device according to one aspect of the disclosure. The replica 100 may include a model implant 110. The model implant 110 may be formed of a lightweight, durable material such that the model implant 110 will not degrade after use. For example, the model implant may be formed of a metal, such as aluminum or stainless steel. In another example, the model implant may be formed of a polymer such as plastic, nylon, radel, polycarbonate, ABS or any combination thereof. The model implant may be coated with a surface coating, such as chromium, or may be colored to resemble a prosthetic device. The model implant 110 may be a model of any type of prosthetic device capable of being implanted into a human body, and may be sized and shaped to conform with any portion of the human body.

In one example, the model implant 110 may be a replica of a implantable femoral prosthesis, such as a unicondylar or bicondylar implant. The model implant 110 may include curved surfaces 112 and 114 that may correspond to the natural curvature of the condyles of a human femur. In one example, the curved surfaces 112 and 114 may correspond to articular surfaces of the implantable prosthetic device represented by the replica 100.

The curved surface 112 may have a first cutout 116 formed therein, and the first cutout 116 may be adapted to receive an insert 118. The first cutout 116 may be a channel of any size, and in one example may be approximately 3.65 cm long, 6.5 cm wide, and 3.75 mm deep. Of course, any dimensions may be used for the first cutout 116. In one example, the insert 118 may have identical dimensions to the first cutout 116 to ensure a secure fit of the insert 118 within the first cutout 116. The insert 118 may be formed of the same, different, or some combination of the material used to form the model implant 110. Although the first cutout 116 is depicted as being formed on the curved surface 112, the first cutout 116 may alternatively be formed on the curved surface 114. In another alternative, each of the curved surfaces 112 and 114 may include a cutout portion formed therein.

While the first cutout 116 is depicted above as a channel formed within the model implant 110, the first cutout 116 may be any type of cutaway portion of the model implant 110. For example, the first cutout 116 may be a removed façade, or a portion of a removed façade, of the model implant 110. In this way, the first cutout 116 may be a partially enclosed channel, or may be completely unenclosed.

The insert 118 may be removably engaged with the first cutout 116 by any affixation method. For example, the insert 118 may include a connection interface on a surface thereof that engages with a corresponding connection interface formed within the first cutout 116. For example, the first cutout 116 may include a hole that corresponds with a peg disposed on the insert 118. In another example, the first cutout 116 may include a hole and the insert 118 may include a peg. In yet another example, the first cutout 116 and the insert 118 may include corresponding magnetic members that creative an attractive force between the first cutout 116 and the insert 118. The attractive force may securely engage the insert 118 with the first cutout 116. Any other removable affixation method may be used to removably engage the insert 118 with the first cutout 116. For example, the insert 118 may snap fit within the first cutout 116. When the insert 118 is engaged with the first cutout 116, the curved surface 112 may form an uninterrupted surface such that a portion of the curved surface 112 is formed by a surface of the insert 118. In this way, a surface of the insert 118, as well as the now uninterrupted curved surface 112, may correspond to a portion of an articular surface of the implantable prosthetic device. For example, where a surface of the insert forms an arc of a circle, the curved surface 112 of the model implant 110 may similarly form an arc of a circle.

The model implant 110 may include a base portion 120 and an attachment 130 that may engage and cooperate to form the model implant 110. The first cutout 116 may be formed on the curved surface 112 that is part of the attachment 130. In another example, the first cutout 116 may be formed on curved surface 114 and may not be part of the attachment 130. In yet another example, the model implant 110 may include two attachments 130, such that each of the curved surfaces 112 and 114 are formed on a respective attachment. The base portion 120 and attachment 130 will be discussed in greater detail below in the context of FIG. 3.

Figure 4:
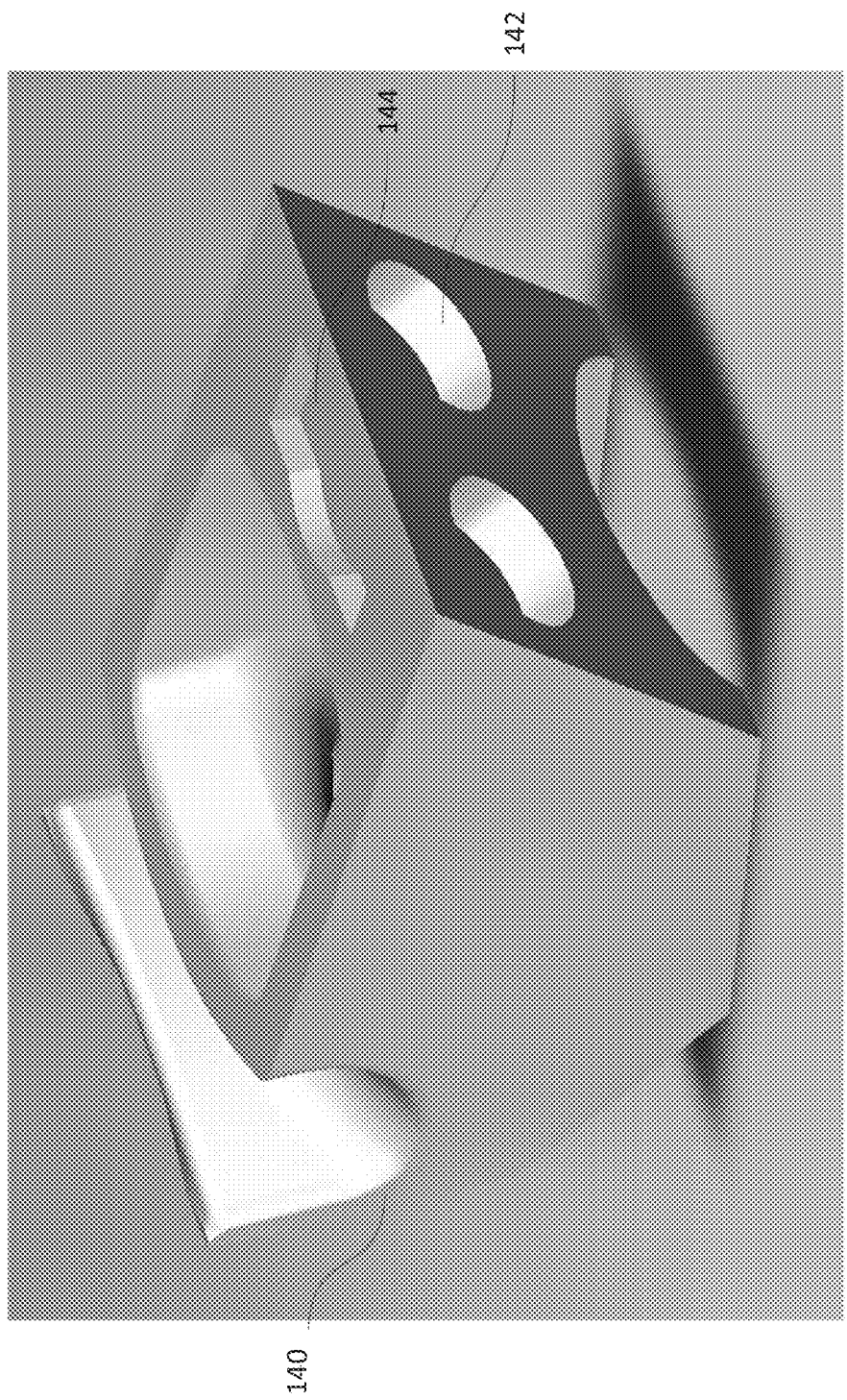
FIG. 4 illustrates a first model implant component according to one aspect of the disclosure.
Figure 5:
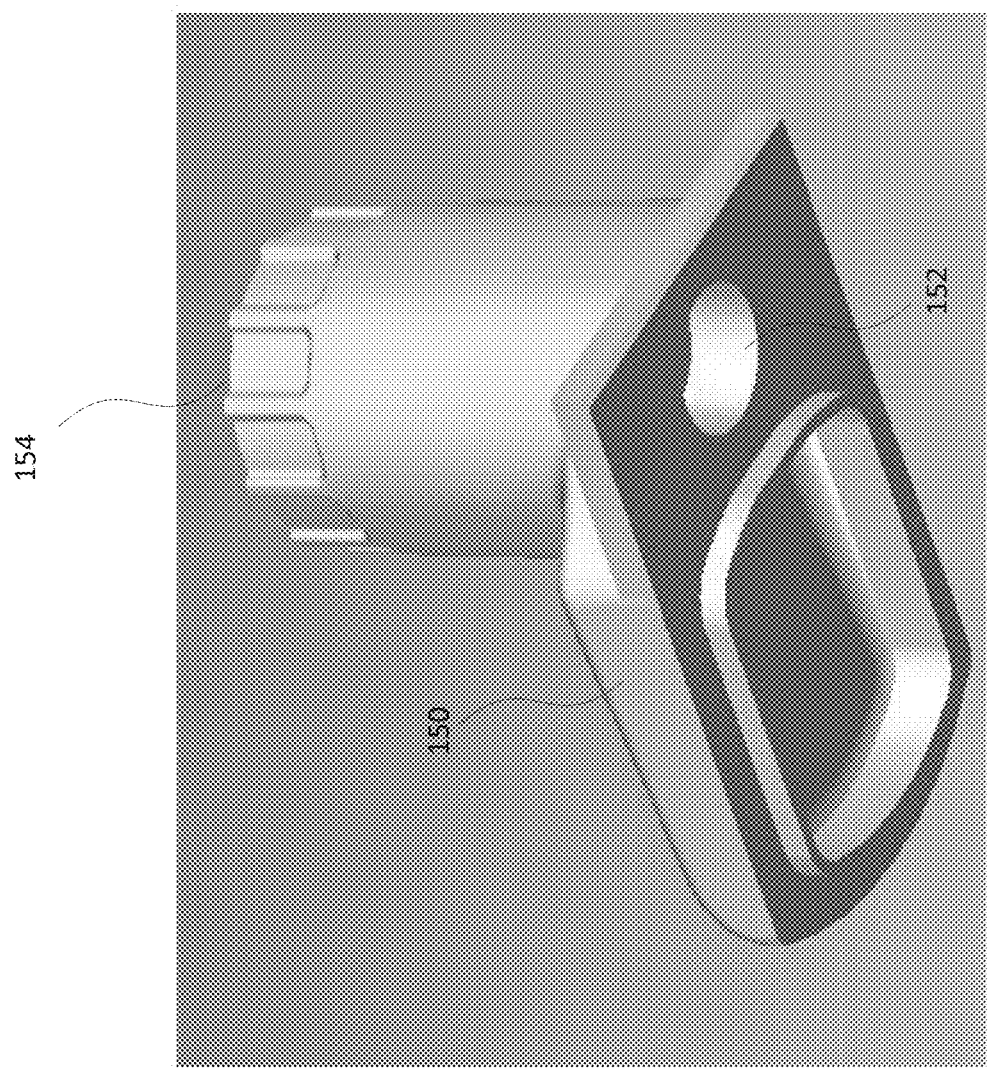
FIG. 5 illustrates a second model implant component according to one aspect of the disclosure.

The replica 100 may also include a first model implant component 140 and a second model implant component 150, as shown in FIGS. 4 and 5, respectively. These components 140 and 150 may be formed of the same, different, or some combination of the material used to form the model implant 110. In one example, the components 140 and 150 may be additional components capable of engaging with one another and/or with the model implant 110 and will be discussed in greater detail below.

Figure 2A:
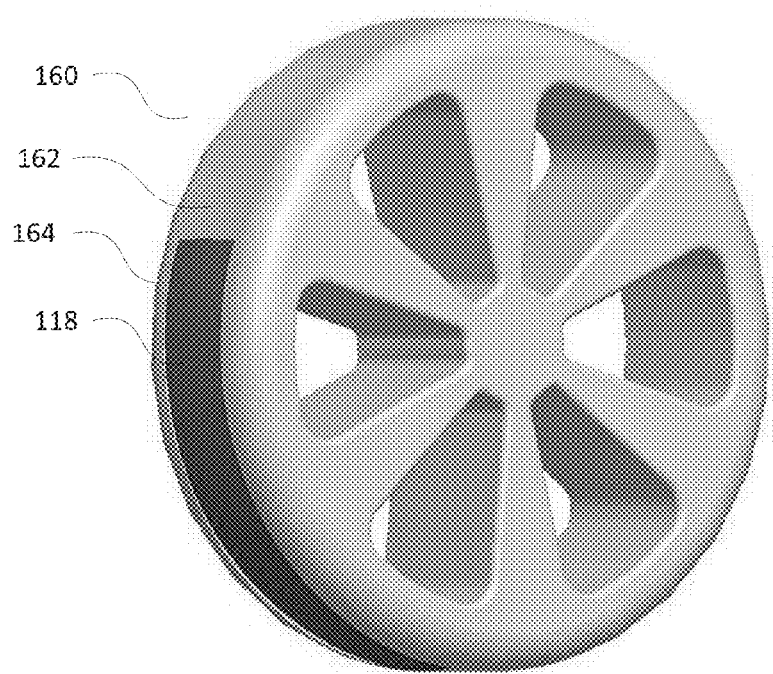
FIGS. 2A and 2B illustrate a geometric tool according to one aspect of the disclosure.
Figure 2B:
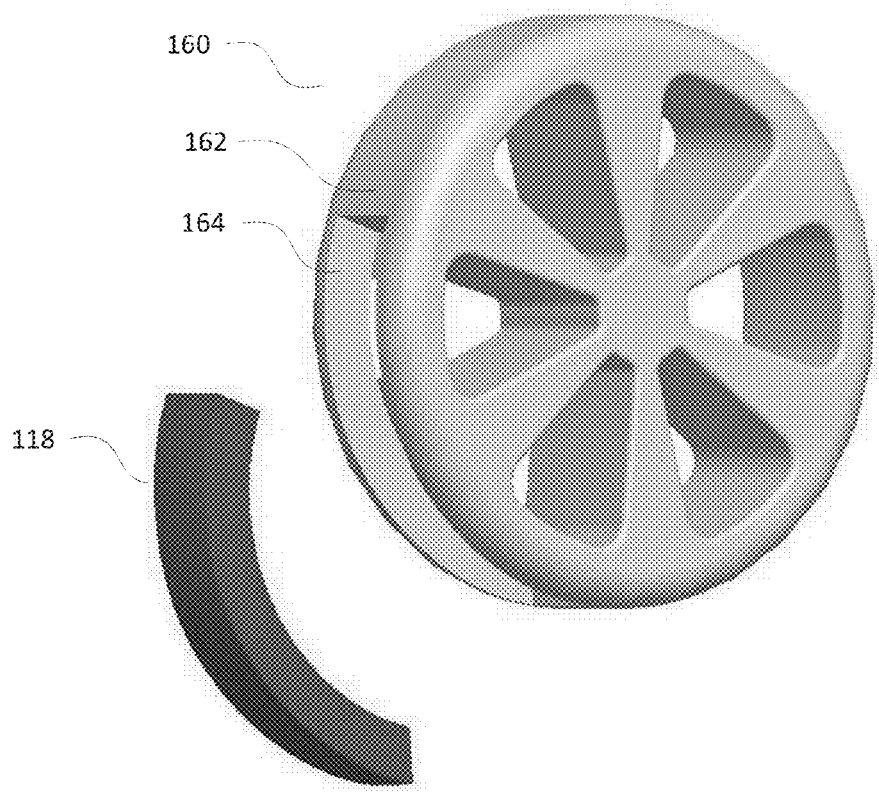

FIGS. 2A and 2B illustrate a geometric tool 160 according to one aspect of the disclosure. The geometric tool 160 may engage with the insert 118 to demonstrate the geometric shape of the insert 118 and the curved surface 112. The geometric tool 160, along with the model implant 110, may be provided as a kit for replicating an implantable prosthetic device. The kit may also include additional components of the replica 100, such as the first model implant component 140, the second model implant component 150, and the spacer component 170. The kit may be provided in a container, such as packaging or a box.

The geometric tool 160 may be in the shape of a cylinder, e.g., a wheel, having a radius of approximately 20 mm and a depth of 12.5 mm. In another example, the geometric tool may be another shape, such as ovular, elliptical, or parabolic. The geometric tool 160 may be any geometric shape, and may have rounded edges. The geometric tool 160 may be formed of the same, different, or some combination of the material used to form the model implant 110.

The geometric tool 160 may have a curved surface 162 that corresponds to at least one of the curved surfaces 112 and 114. The geometric tool 160 may also include a second cutout 164 that corresponds to the first cutout 116. In this way, the geometric configuration of the second cutout 164 may be substantially identical to the geometric configuration of the first cutout 116. The insert 118 may engage with the geometric tool 160 within the second cutout 164, such that, when engaged with the insert 118, the curved surface 162 forms an uninterrupted surface. The insert 118 may engage with the second cutout 164 in the same way as the insert 118 engages with the first cutout 116. In this way, the insert 118 may be interchangeably engaged between the model implant 110 and the geometric tool 160. In the example where the geometric tool 160 is cylindrical, the geometric tool 160 may be capable of rolling when the insert 118 is engaged with the curved surface 162. Rolling the geometric tool 160 may demonstrate to a potential consumer that the curved surface 162, as well as the curved surface 112 with which the insert 118 may engage, are continuously curved and circular. Although the geometric tool 160 is depicted as having a second cutout 164, the geometric tool 160 may include multiple cutouts.

While the insert 118 is described as being curved in one plane, any type of curvature can be utilized as is necessary for the particular implant. For instance, the insert 118 may be curved in the anterior-posterior plane, the medial-lateral plane, the superior-inferior plane, or any other plane. In addition, the insert 118 may be defined by a complex curvature.

Figure 3A:
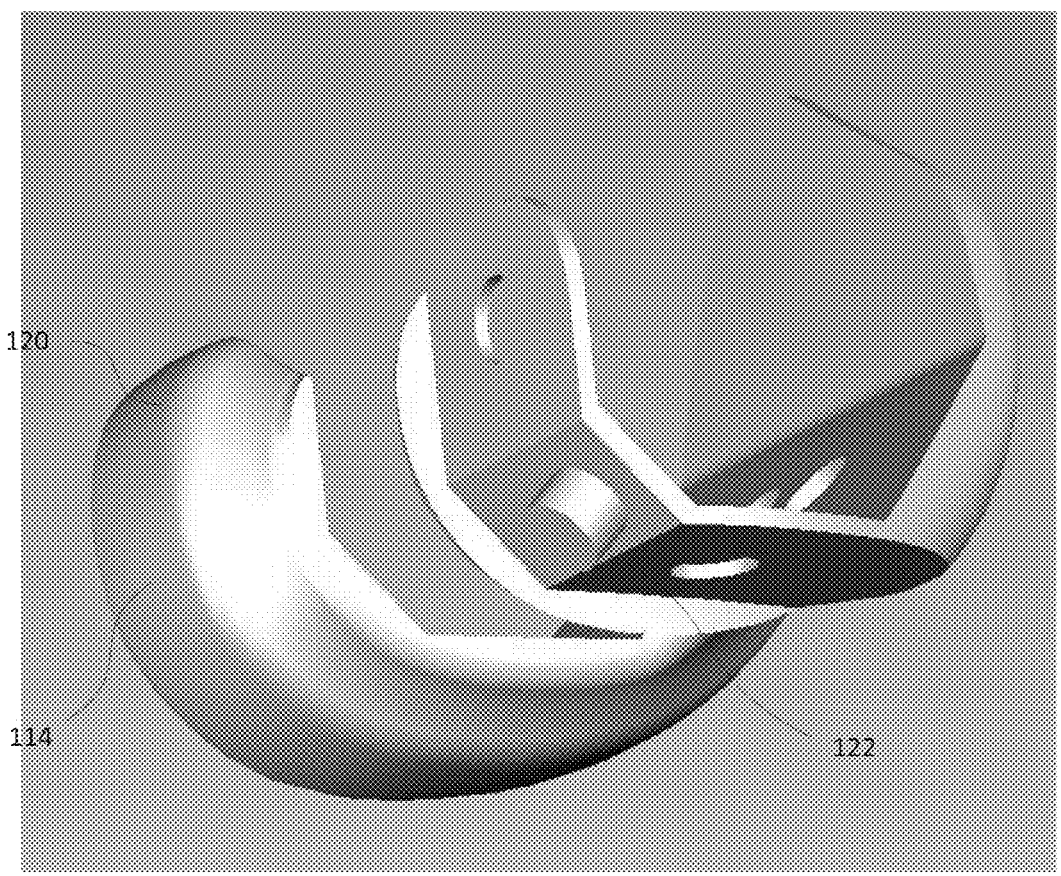
FIGS. 3A and 3B illustrate the base portion and the attachment portion, respectively, of the model implant according to one aspect of the disclosure.
Figure 3B:
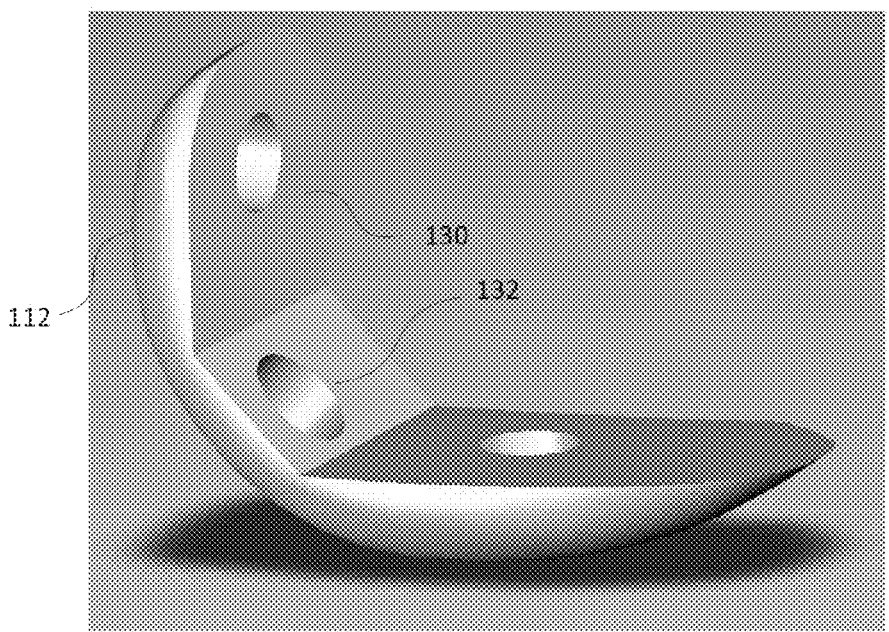

FIGS. 3A and 3B illustrate the base portion 120 and the attachment portion 130, respectively, of the model implant 110 according to one aspect of the disclosure. The base portion 120 and the attachment 130 may engage and cooperate to form the overall shape of the model implant 110. The base portion 120 may include an interface 122 that corresponds to an interface 132 on the attachment 130. The interfaces 122 and 132 may engage, allowing the base portion 120 and the 130 to engage with one another. The base portion 120 and the attachment 130 may be removably, semi-permanently, or permanently coupled. Although interfaces 122 and 132 are depicted above, the base portion 120 and attachment 130 may be coupled by any other attachment method, such as an adhesive or by including pegs, slots, or channels that engage with one another. Alternatively, the base portion 120 and the attachment 130 may be press fit. In one example, the base portion 120 may comprises a portion of a bicondylar knee implant, and the attachment 130 comprises a unicondylar knee implant engageable with the bicondylar implant. Although model implant 110 is depicted as having a base portion 120 and an attachment 130, the model implant 110 may comprise a unitary implant that does not include a separate base portion 120 and attachment 130.

The base portion 120 may also include another interface 124 capable of engaging with an additional component, such as a first model implant component 140, as illustrated in FIG. 4 according to one aspect of the disclosure. The first model implant component 140 may be any type of implant component capable of engaging with the model implant 110. For example, the first model implant component 140 may be a component that facilitates installation of an implantable prosthesis or that supports the surrounding anatomy after a prosthesis is implanted. As illustrated in FIG. 4, the first model implant component 140 may be a cam that engages with the model implant 110. The first model implant component 140 may engage with the model implant 110 via interface 142. For example, the interface 142 may engage with a corresponding interface of the model implant 110, such as the interface 124 disposed on the base portion 120.

The first model implant component 140 may include an additional interface 144 that is capable of engaging with an additional component, such as the second model implant component 150, as illustrated in FIG. 5 according to one aspect of the disclosure. The second model implant component 150 may be any type of implant component capable of engaging with the model implant 110 and/or the first model implant component 140. For example, the second model implant component 150 may be a component that facilitates installation of an implantable prosthesis or that supports the surrounding anatomy after a prosthesis is implanted. As illustrated in FIG. 5, the second model implant component 150 may be a post that engages with the first model implant component 140. The second model implant component 150 may include an interface 152 that is engageable with a corresponding interface of the first model implant component 140, such as interface 144. The second model implant 150 may include a hole 154 that is capable of engaging with a rod, such as a femoral stem, that may be implanted within a human femur. In this way, the implantable prosthesis represented by the replica system may be secured within a human knee.

In addition to the components described above, other components may be provided as necessary to replicate other desired aspects of an implantable prosthetic device.

Figure 6:
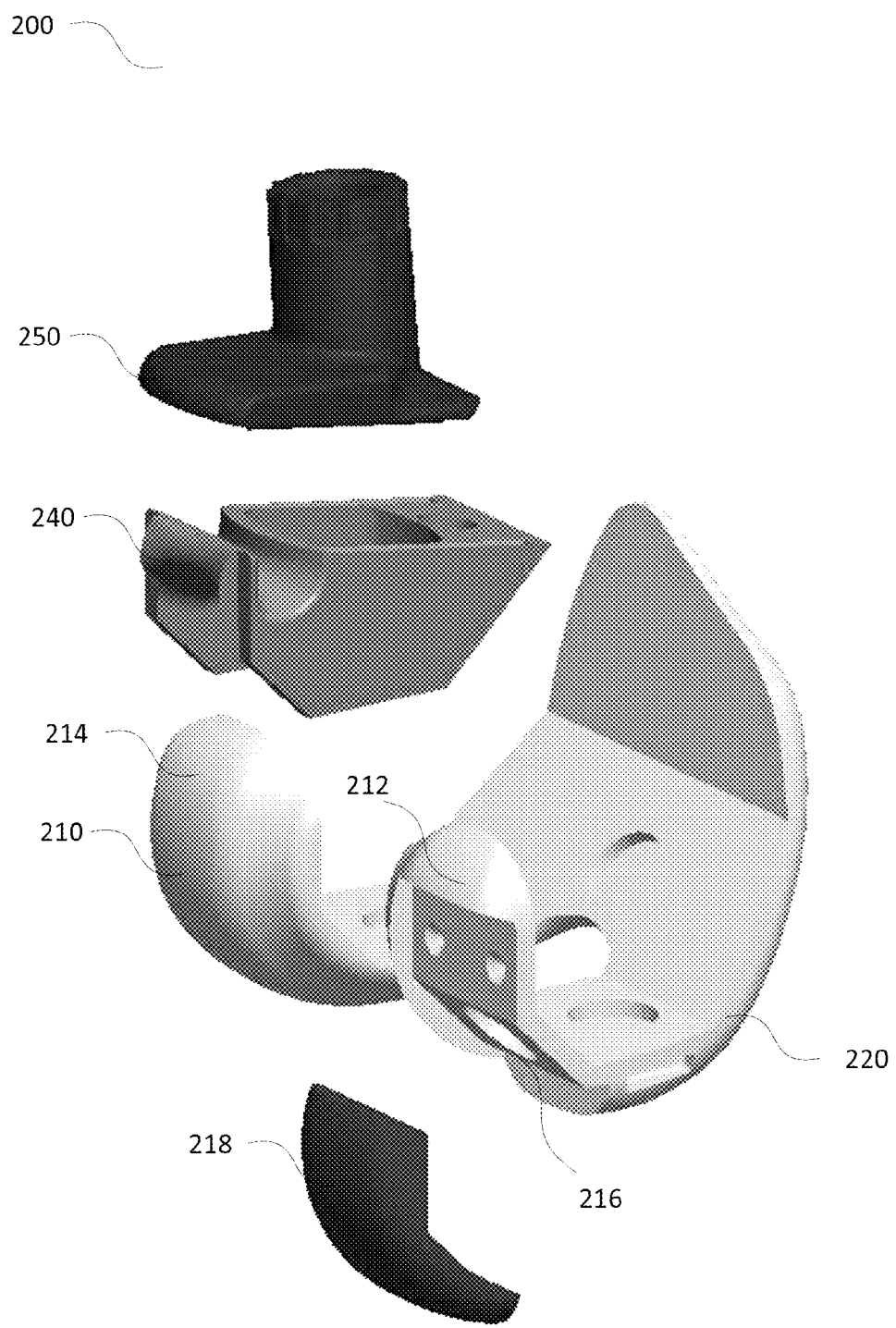
FIG. 6 illustrates a illustrates an exploded view of a replica of an implantable prosthetic device according to another aspect of the disclosure.

FIG. 6 illustrates an exploded view of a replica 200 of an implantable prosthetic device according to another aspect of the disclosure. The replica 200 may be similar to the replica 100 describe above. For example, the replica 200 may include a model implant 210. The model implant 210 may include curved surfaces 212 and 214. The model implant 210 may include a base portion 220. In this example, a first cutout 216 may be formed in the base portion 220 of the model implant 210. The first cutout 216 may be a cutaway portion in the curved surface 212. In this way, the first cutout 216 may be a partially enclosed channel. In this example, the first cutout 216 may have greater dimensions than the first cutout 116 described above. The first cutout 216 may be of any size, and in one example, the dimensions of the first cutout 216 may be 3.7 cm length×2 cm width×5 mm depth. The insert 218 may also be any size, and may have substantially the same dimensions as the first cutout 216. The replica 200 may also include a first model implant component 240 and a second model implant component 250.

As described above, the insert 218 may engage with the first cutout 216, such that the curved surface 212 may form an uninterrupted surface. In one example, a portion of the curved surface 212 may correspond to an arc of a circle.

Figure 7:
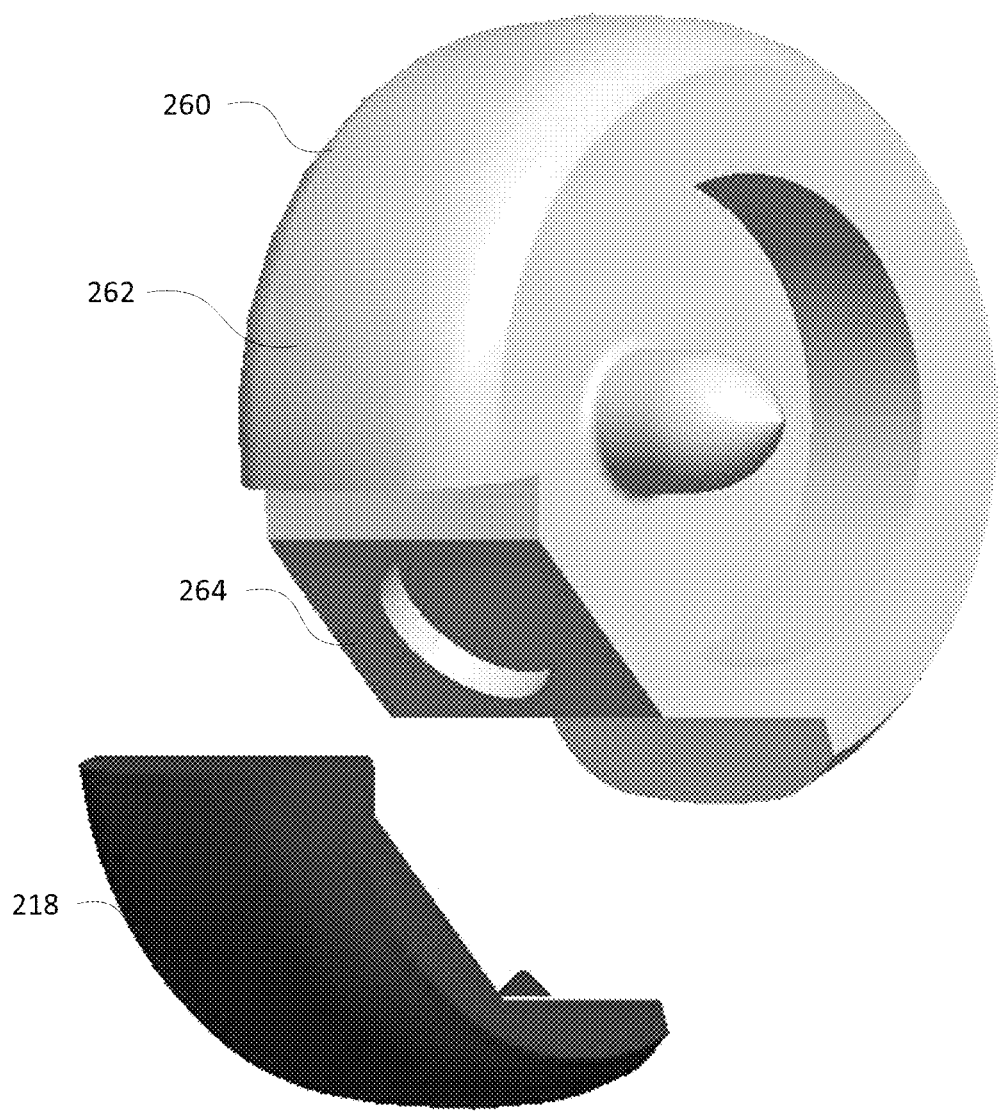
FIG. 7 illustrates a geometric tool according to another aspect of the disclosure.

FIG. 7 illustrates a geometric tool 260 according to another aspect of the disclosure. In this example, the geometric tool 260 may be similar to the geometric tool 160 described above. For example, the geometric tool 260 may include a curved surface 262, at least a portion of which may correspond to one of the curved surfaces 212 and 214. The geometric tool 260 may also include a second cutout 264 that may correspond to the first cutout 216. In this way, the insert 218 may engage with cutout 264 of the geometric tool 260. The insert 218 may interchangeably engage with the first cutout 216 and the second cutout 264. When the insert 218 is engaged with the geometric tool 260, the curved surface 262 may form an uninterrupted surface.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit for replicating an implantable prosthetic device, comprising:
   a model implant including a first curved surface curved about a first diameter with a first arc length, the first curved surface having a first cutout;
   a geometric tool having a second curved surface on an exterior of the geometric tool curved about a second diameter with a second arc length, the second curved surface having a second cutout such that the second cutout forms a hole in the second curved surface,
      wherein the first diameter is equal to the second diameter, and
      wherein the first arc length is substantially equal to the second arc length; and
   an insert configured to be engaged interchangeably with either the first cutout or the second cutout,
      wherein the first curved surface with the insert disposed therein completes a first articulation surface and the second curved surface with the insert disposed therein completes a second articulation surface; and wherein the geometric tool, when engaged with the insert, forms a wheel, the exterior surface of the geometric tool, when the tool is engaged with the insert, defining an uninterrupted and complete substantially circular circumference of the wheel.

2. The kit of claim 1, wherein the first curved surface corresponds to the first articular surface of the implantable prosthetic device.

3. The kit of claim 2, wherein the insert defines an insert surface that corresponds to a portion of the first articular surface of the implantable prosthetic device.

4. The kit of claim 3, wherein at least a portion of the insert surface coincides with an arc of a circle.

5. The kit of claim 1, further comprising: a first model implant component engageable with the model implant.

6. The kit of claim 5, further comprising a second model implant component engageable with the first model implant component.

7. The kit of claim 6, wherein the model implant, when engaged with the insert, is a replica of a femoral prosthesis, and wherein the first model implant component includes a cam.

8. The kit of claim 6, wherein the model implant, when engaged with the insert, is a replica of a femoral prosthesis, and wherein the second model implant component includes a post configured to engage with a femoral stem.

9. The kit of claim 1, wherein the model implant comprises a base portion and an attachment removably coupled to the base portion.

10. The kit of claim 9, wherein the base portion comprises at least a portion of a bicondylar knee implant.

11. The kit of claim 10, wherein the attachment comprises a unicondylar knee implant engageable with the bicondylar implant.

12. A kit for replicating an implantable prosthetic device, comprising:
    a model implant comprising a base portion and an attachment, the attachment including a first curved surface curved about a first diameter with a first arc length, the first curved surface having a first cutout;
    a geometric tool having a second curved surface on an exterior of the geometric tool curved about a second diameter with a second arc length, the second curved surface having a second cutout such that the second cutout forms a hole in the second curved surface,
       wherein the first diameter is equal to the second diameter, and
       wherein the first arc length is substantially equal to the second arc length;
    an insert configured to be engaged interchangeably with either the first cutout or the second cutout,
       wherein the first curved surface with the insert disposed therein completes a first uninterrupted articulation surface and the second curved surface with the insert disposed therein completes a second uninterrupted articulation surface;
    a first model implant component engageable with the model implant; and
    a second model implant component engageable with the first model implant component; and wherein the geometric tool, when engaged with the insert, forms a wheel, the exterior surface of the geometric tool, when the tool is engaged with the insert, defining an uninterrupted and complete substantially circular circumference of the wheel.

13. The kit of claim 12, wherein the model implant, when engaged with the insert, is a replica of a femoral prosthesis.

* * * * *